United States Patent [19]
Griebel et al.

[11] Patent Number: 6,157,034
[45] Date of Patent: Dec. 5, 2000

[54] FLEXIBLE MULTI-PURPOSE MODULAR ASSEMBLY FOR A FAMILY OF PGNAA BULK MATERIAL ANALYZERS

[75] Inventors: Craig A. Griebel; Michael J. Hurwitz; Raymond J. Proctor; James P. Stronski; Kim-Chinh Tran; Siaka Yusuf, all of San Diego, Calif.

[73] Assignee: Gamma-Metrics

[21] Appl. No.: 09/109,484

[22] Filed: Jul. 2, 1998

[51] Int. Cl.[7] .................................................. G01N 23/222
[52] U.S. Cl. .................................... 250/358.1; 250/359.1; 376/159
[58] Field of Search .............................. 250/358.1, 359.1, 250/360.1, 390.01, 390.04, 390.06, 391, 269.6; 376/159, 157

[56] References Cited

U.S. PATENT DOCUMENTS

| | | |
|---|---|---|
| 3,278,747 | 10/1966 | Ohmart . |
| 3,794,843 | 2/1974 | Chen . |
| 4,028,267 | 6/1977 | Christell et al. . |
| 4,428,902 | 1/1984 | Murray . |
| 4,582,992 | 4/1986 | Atwell et al. ............................ 250/359.1 |
| 4,694,165 | 9/1987 | Proctor et al. .......................... 250/252.1 |
| 4,929,895 | 5/1990 | Typpo ........................................ 324/231 |
| 5,162,096 | 11/1992 | Gozani . |
| 5,315,124 | 5/1994 | Goss et al. ............................. 250/497.1 |
| 5,396,071 | 3/1995 | Atwell et al. . |
| 5,539,788 | 7/1996 | Ruddy et al. ............................ 376/159 |
| 5,732,115 | 3/1998 | Atwell et al. ............................ 376/157 |

FOREIGN PATENT DOCUMENTS

| | | |
|---|---|---|
| 42108/78 | 11/1978 | Australia . |
| 459648 A1 | 4/1991 | European Pat. Off. .......... G01V 5/00 |
| WO 9743625 | 11/1997 | WIPO ........................... G01N 23/222 |

OTHER PUBLICATIONS

"Geoscan Through Belt Analyzer," Mineral Controls Instrumental Limited: 1995 (estimated).

*Primary Examiner*—Constantine Hannaher
*Attorney, Agent, or Firm*—Edward W. Callan

[57] ABSTRACT

A modular assembly for a bulk material includes container modules defining at least one radiation source cavity, at least one radiation detector channel and a passageway disposed for enabling passage of the conveyor belt through an activation region; and radiation shielding material disposed within the container means. A lower primary module contains a first portion of the radiation shielding material and defines either the radiation source cavity or the radiation detector channel. An upper primary module contains a second portion of radiation shielding material and defines the other of either the radiation source cavity or the radiation detector channel. A set of replaceable side modules contain additional portions of the radiation shielding material. The lower primary module, the upper primary module and the replaceable side modules are so shaped that the passageway is delimited by placement of side modules upon the lower primary module and placement of the upper primary module upon side modules; and portions of the replaceable side modules are shaped for delimiting the sides of a trough that is contoured for accommodating passage of the conveyor belt through the activation region. Replaceable liners of neutron moderating and/or absorbing and/or reflecting material may be placed adjacent the passageway and adjacent the side modules and/or the lower module and/or the upper module for further delimiting the passageway and/or the sides of the trough. The assembly can be modified for use with large ranges of conveyor belt sizes and shapes by replacing the replaceable side modules and/or the replaceable liners.

54 Claims, 6 Drawing Sheets

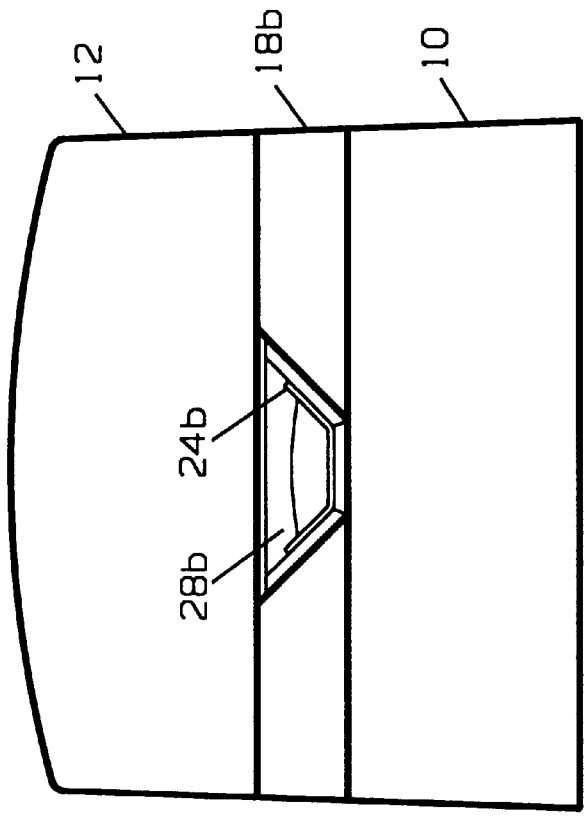
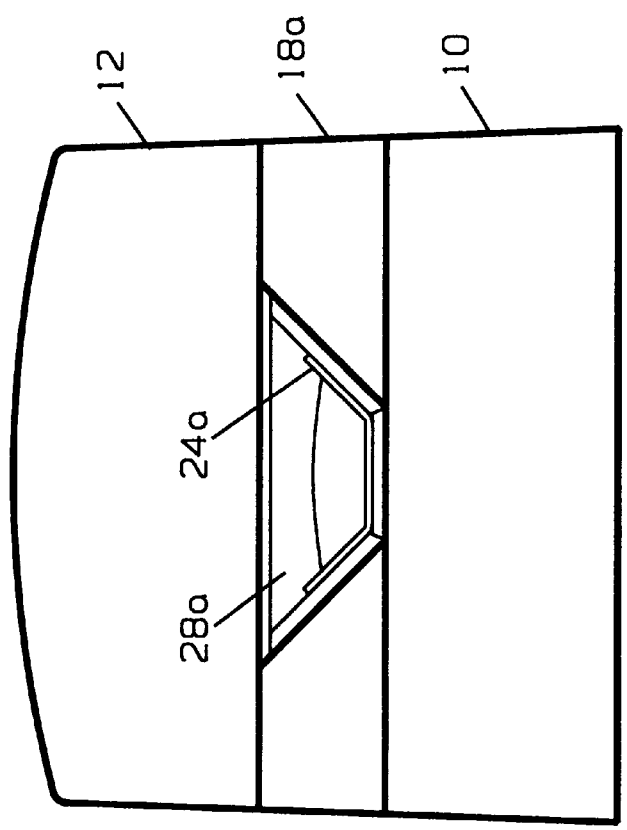

FLEXIBLE MULTI-PURPOSE MODULAR ASSEMBLY FOR A FAMILY OF PGNAA BULK MATERIAL ANALYZERS

BACKGROUND OF THE INVENTION

The present invention generally pertains to bulk material analyzers and is particularly directed to an improved modular assembly for bulk material analyzers of the type in which the bulk material is transported through an analysis region located between a radiation source and a radiation detector in the bulk material analyzer. The analysis region is usually referred to herein as an activation region.

Bulk material analyzers are used to measure the elemental content of bulk materials. In one type of bulk material analyzer, the radiation source includes one or more neutron sources and the radiation detector includes one or more gamma-ray detectors that produce signals which are processed to provide a measurement of the elemental content of the bulk material. When the bulk material is bombarded with neutrons, secondary emissions of gamma-rays are produced from the bulk material. Different characteristic spectra of gamma-ray energy are produced from different elements of the bulk material. By processing the detected signals that are indicative of the gamma-ray spectrum a measurement is provided of the elemental content of the bulk material. This measurement process is known as prompt gamma-ray neutron activation analysis (PGNAA). In addition to containing the radiation source and the radiation detector, the bulk material analyzer assembly necessarily includes a large quantity of radiation shielding material in order to protect persons using the bulk material analyzer from harmful doses of radiation. The required quantity of radiation shielding is such that the bulk material analyzer assembly is so large that the assembly is not easily handled for transportation from one site to another.

U.S. Pat. No. 5,396,071 to Atwell et al. describes a modular assembly for a PGNAA bulk material analyzer of the type in which bulk material is transported on a conveyor belt through an activation region located between at least one radiation source and at least one radiation detector within the bulk material analyzer. Such assembly includes container means that include a lower primary module containing radiation shielding material and defining either at least one radiation source cavity or at least one radiation detector cavity; and an upper primary module containing radiation shielding material and defining the other of either the at least one radiation source cavity or the at least one radiation detector cavity that is not defined by the lower primary module. The lower primary module and the upper primary module are so shaped that the passageway is delimited by placement of the upper primary module upon the lower primary module; and portions of the lower primary module are shaped for delimiting the sides of a trough that is contoured for accommodating passage of the conveyor belt through the activation region. The trough-delimiting portions of the lower module are inclined outwardly from the bottom of the passageway to accommodate a passage on a conveyor belt having a complementary contour.

The modular assembly described in the aforementioned U.S. Pat. No. 5,396,071 is easily handled for transportation and readily installed about a conveyor belt that is used for transporting the bulk material that is to be analyzed, such that the analyzer can be installed in an existing processing line without having to cut or otherwise disassemble the conveyor belt. As the so-described modular assembly has been applied to a wide range of applications, it has been found that a given embodiment thereof can be used with only small ranges of conveyor belt sizes and shapes. Although small differences in conveyor belt sizes and shapes have been compensated for by placing neutron-moderating-material liners of selected sizes and shapes on the respective modules adjacent the passageway, when such differences are not small it has been necessary to provide an entirely different bulk material analyzer assembly including a passageway and a trough having dimensions and shapes that are appropriate accommodating the passage of the conveyor belt.

SUMMARY OF THE INVENTION

The present invention provides an improved modular assembly for a bulk material analyzer that can be modified for use with large ranges of conveyor belt sizes and shapes.

In one aspect, the present invention provides an assembly for a bulk material analyzer of the type in which bulk material is transported on a conveyor belt through an activation region located between at least one radiation source and at least one radiation detector within the bulk material analyzer, said assembly comprising container means including means for retaining at least one radiation detector, and defining at least one radiation source cavity and a passageway disposed for enabling passage of a conveyor belt through an activation region located between the at least one radiation source cavity and the means for retaining at least one radiation detector; and radiation shielding material disposed within the container means; wherein the container means comprise a lower primary module containing a first portion of the radiation shielding material and either defining said at least one radiation source cavity or including said means for retaining at least one radiation detector; an upper primary module containing a second portion of radiation shielding material and either defining or including the other of either said at least one radiation source cavity or said means for retaining at least one radiation detector that is not defined or included respectively in the lower primary module; and a set of replaceable side modules containing additional portions of the radiation shielding material; wherein the lower primary module, the upper primary module and the replaceable side modules are so shaped that the passageway is delimited by placement of side modules upon the lower primary module and placement of the upper primary module upon at least some of the placed side modules; and wherein portions of at least a pair of the replaceable side modules are shaped for delimiting the sides of a trough that is contoured for accommodating passage of the conveyor belt through the activation region. In some embodiments, the assembly may further include replaceable liners of neutron moderating and/or absorbing and/or reflecting material placed adjacent the passageway and adjacent the side modules and/or the lower module and/or the upper module for further delimiting the passageway and/or the sides of the trough and for controlling the neutron distribution and thereby the uniformity of measurement sensitivity throughout the portion of the activation region that is occupied by the bulk material.

Accordingly, the bulk material analyzer assembly of the present invention can be modified for use with large ranges of conveyor belt sizes and shapes, of bulk material depths, and/or proximity of the radiation detector(s) to the bulk material merely by replacing the less complex and less expensive replaceable side modules and/or the replaceable liners. In some instances it is desirable to adjust the depth of the bulk material and/or the proximity of the radiation detector(s) to the bulk material in order to enhance the uniformity of measurement sensitivity throughout the portion of the activation region that is occupied by the bulk material.

The present invention is not limited to bulk material analyzer assemblies of the type in which the bulk material is transported through the activation region on a conveyor belt, but also is applicable to assemblies of the type in which the bulk material is transported through the activation region by other means, such as a chute or a slide. Accordingly, the present invention provides an assembly for a bulk material analyzer of the type in which bulk material is transported through an activation region located between at least one radiation source and at least one radiation detector within the bulk material analyzer, said assembly comprising container means including means for retaining at least one radiation detector, and defining at least one radiation source cavity and a passageway disposed for enabling passage of bulk material through an activation region located between the at least one radiation source cavity and the means for retaining at least one radiation detector; and radiation shielding material disposed within the container means; wherein the container means comprise a first primary module containing a first portion of the radiation shielding material and either defining said at least one radiation source cavity or including said means for retaining at least one radiation detector; an second primary module containing a second portion of radiation shielding material and either defining or including the other of either said at least one radiation source cavity or said means for retaining at least one radiation detector that is not defined or included respectively in the first primary module; and a set of replaceable side modules containing additional portions of the radiation shielding material; wherein the first primary module, the secondary primary module and the replaceable side modules are so shaped that the passageway is delimited by placement of the side modules between the first primary module and the second primary module.

In another aspect, the present invention provides an assembly for analysis of bulk material moving through an analysis region located between at least one radiation source and at least one radiation detector, the assembly comprising a first module containing radiation shielding material and including means for retaining the at least one radiation source; a second module containing radiation shielding material and including means for retaining the at least one radiation detector; and at least two replaceable modules, each containing radiation shielding material, sandwiched between the first module and the second module to separate the first module from the second module, with the at least two replaceable modules being separated, to delimit a passageway for movement of the bulk material through the analysis region. In some embodiments, the assembly may further include at least one replaceable liner placed on a said module to further delimit the passageway, and the at least one replaceable liner may include a material having a characteristic of at least one of neutron moderating, neutron absorbing or neutron reflecting.

The present invention further provides an assembly for a bulk material analyzer of the type in which bulk material is transported on a conveyor belt through an activation region located between at least one radiation source and at least one radiation detector within the bulk material analyzer, container means include means for retaining at least one radiation detector, and define at least one radiation source cavity and a passageway disposed for enabling passage of a conveyor belt through an activation region located between the at least one radiation source cavity and the means for retaining at least one radiation detector; and radiation shielding material is disposed within the container means; and the container means comprise a lower primary module, containing a first portion of the radiation shielding material and either defining said at least one radiation source cavity or including said means for retaining at least one radiation detector; and an upper primary module containing a second portion of radiation shielding material and either defining or including the other of either said at least one radiation source cavity or said means for retaining at least one radiation detector that is not defined or included respectively in the lower primary module; said assembly comprising a set of replaceable side modules containing additional portions of the radiation shielding material; wherein the replaceable side modules are so shaped in relation to the lower primary module and the upper primary module that the passageway is delimited by placement of side modules upon the lower primary module and placement of the upper primary module upon at least some of the placed side modules; and wherein portions of at least a pair of the replaceable side modules are shaped for delimiting the sides of a trough that is contoured for accommodating passage of the conveyor belt through the activation region.

In another aspect of the present invention, it has been discovered that when a PGNAA bulk material analyzer utilizing a conveyor belt to transport the bulk material through the activation region is used for analyzing the composition of bulk material that includes more than four percent hydrogen by weight, the uniformity of measurement sensitivity throughout the portion of the activation region that is occupied by the bulk material is enhanced by disposing the neutron source(s) above the belt and disposing the gamma-ray detector(s) below the belt. This is because the material typically used in conveyor belts has such a high proportion of hydrogen that when the conveyor belt is disposed between the neutron source and the activation region, the neutron moderating effect of the hydrogen in the conveyor belt so combines with the higher neutron moderating effect resulting from the higher hydrogen content of the bulk material as to make it more difficult to achieve uniformity of measurement sensitivity throughout the portion of the activation region that is occupied by the bulk material.

According to this aspect, the present invention provides an assembly for a bulk material analyzer of the type in which bulk material is transported on a conveyor belt through an activation region located between at least one neutron source and at least one gamma-ray detector within the bulk material analyzer, and in which signals produced by the gamma-ray detector in response to gamma-rays secondarily emitted from the bulk material in response to bombardment of neutrons are processed in order to determine the elemental content of the bulk material, said assembly comprising container means including means for retaining at least one radiation detector, and defining at least one radiation source cavity and a passageway disposed for enabling passage of a conveyor belt through an activation region located between the at least one radiation source cavity and the means for retaining at least one radiation detector; and radiation shielding material disposed within the container means; wherein the at least one neutron source cavity is disposed above the passageway; wherein the means for retaining at least one radiation detector is disposed below the passageway; and wherein a neutron reflecting material is disposed between the conveyor belt and the means for retaining at least one radiation detector.

Also according to this aspect, the present invention provides an improved method of analyzing the composition of bulk material having a hydrogen content exceeding four percent by weight, comprising the steps of:

(a) transporting the bulk material on a conveyor belt through an activation region located between at least one neutron source and at least one gamma-ray detector; and (b) processing signals produced by the gamma-ray detector in response to gamma-rays secondarily emitted from the bulk material in response to bombardment of neutrons in order to determine the elemental content of the bulk material, wherein the improvement comprises the steps of:

(c) disposing the at least one neutron source above the conveyor belt;

(d) disposing the at least one gamma-ray detector below the conveyor belt; and (e) disposing a neutron reflecting material between the conveyor belt and the at least one gamma-ray detector.

Additional features of the present invention are described in relation to the detailed description of the preferred embodiments.

BRIEF DESCRIPTION OF THE DRAWING

FIGS. 4A and 4B show a pair of replaceable sets of side modules of different sizes and shapes respectively placed between a given set of a lower primary module and an upper primary module for accommodating the passage of different sizes and shapes of conveyor belts.

DETAILED DESCRIPTION

Figure 1:
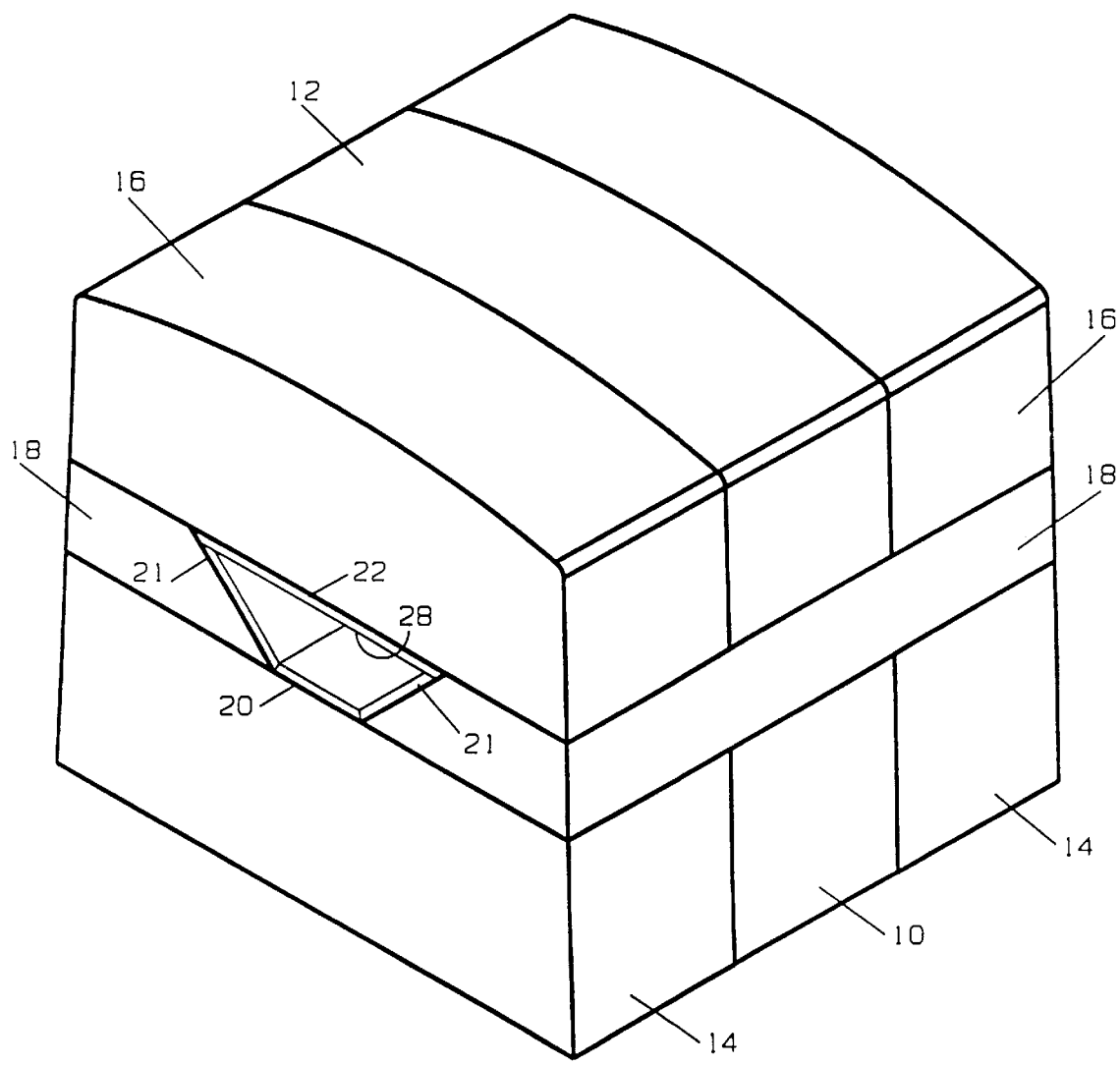
FIG. 1 is a perspective view of a preferred embodiment of a modular bulk material analyzer assembly according to the present invention.
Figure 2:
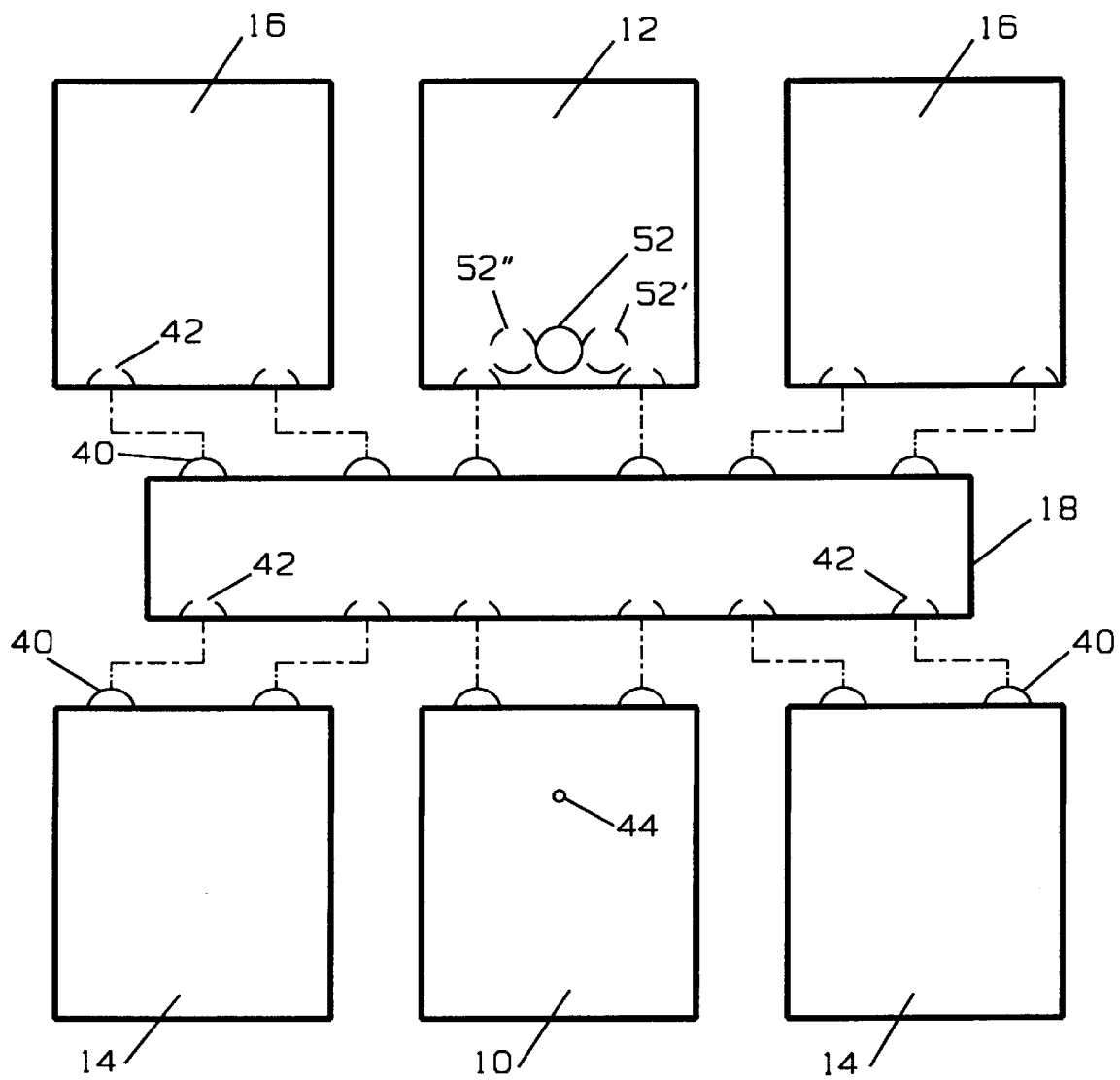
FIG. 2 is an exploded side elevation view of the assembly of FIG. 1 illustrating the placement of the modules with respect to one another.
Figure 3:
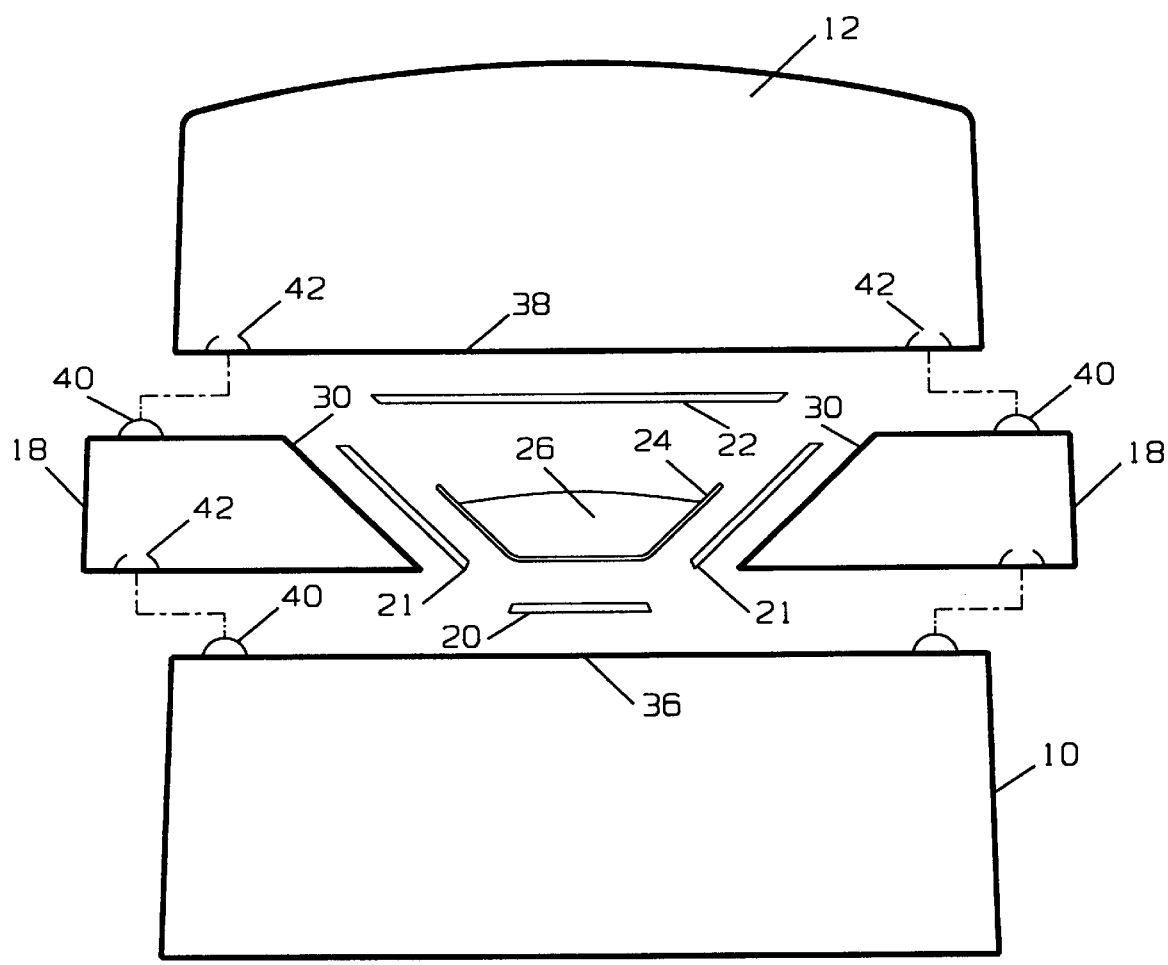
FIG. 3 is an exploded end elevation view of a portion of the assembly of FIG. 1 illustrating the placement of the replaceable side modules and the placement of the replaceable liners with respect to the lower primary module, the upper primary module and the conveyor belt.

Referring to FIGS. 1, 2 and 3, a preferred embodiment of a modular bulk material analyzer assembly according to the present invention includes a lower primary module 10, an upper primary module 12, a pair of lower secondary modules 14, a pair of upper secondary modules 16, a set of replaceable side modules 18 and a set of replaceable liners 20, 21, 22. Each of the modules 10, 12, 14, 16, 18 contains radiation shielding material. The secondary modules 14, 16 are placed upstream and down stream of the primary modules 10, 12 for the purpose of lowering the radiation flux outside of the assembly. The walls of the modules 10, 12, 14, 16, 18 preferably are made of molded fiber reinforced plastic, plastic sheet, or sheet metal. In an alternative embodiment (not shown), instead of a single side module 18 being placed at each side of the passageway, a plurality of smaller, personally portable, differently-dimensioned-and-shaped, side modules of neutron shielding material are placed between the lower primary module 10 and the upper primary module 12 on each side of the passageway 28 in the respective volumes of space otherwise occupied by the side modules 18 in the preferred embodiment shown in the figures of the Drawing.

The lower primary module 10 defines either at least one radiation source cavity or at least one radiation detector channel; and the upper primary module 12 defines the other of either the at least one radiation source cavity or the at least one radiation detector channel that is not defined by the lower primary module 10, as further described below with reference to FIGS. 5 and 6. As seen in FIG. 3, a conveyor belt 24 transports bulk material 26 through an activation region located within a passageway 28 that is defined between the lower primary module 10, the upper primary module 12 and the set of replaceable side modules 18. Each side module 18 preferably extends from the passageway 28 to a plane that includes the outside surfaces of the lower primary module 10 and the upper primary module 12, thereby filling the space between the lower module 10 and upper module 12 except for the space occupied by the passageway 28 and the replaceable liners 20, 21, 22.

The lower primary module 10, the upper primary module 12 and the replaceable side modules 18 are so shaped that the passageway 28 is delimited by placement of the side modules 18 upon the lower primary module 10 and the lower secondary modules 14 and placement of the upper primary module 12 and the upper secondary modules 16 upon the placed side modules 18. Since each side modules 18 has a smaller longitudinal cross-section than that of the lower modules 10, 14 and the upper modules 12, 16 (as seen in FIG. 3), each side module 18 can extend over the entire length of the assembly, as shown in FIG. 2, and still be of a size and weight comparable to those of the respective lower and upper modules; thereby minimizing cost by reducing the number of modules and also providing a more rugged and rigid construction.

Opposing surfaces 30 of the respective replaceable side modules; 18 are shaped for delimiting the sides 32 of a trough 34 that is contoured for accommodating passage of the conveyor belt 24 through the passageway 28. The trough 34 may be shaped to complement the shape of the conveyor belt 24, as shown in FIG. 5, or the trough 34 may be rounded upward from its longitudinal center, and/or have vertical sides (not shown), to accommodate passage of a flat conveyor belt. Also, the bottom of the passageway 28 is delimited by a bottom-of-the-trough portion 36 of the lower primary module 10 and the top of the passageway 28 is delimited by a portion 38 of the upper primary module 12. The trough-delimiting surfaces 30 of the replaceable side modules 12 are inclined outwardly from the bottom of the passageway 28 in order to accommodate the passage of a conveyor belt 24 that has outwardly inclined side walls. The angle of inclination of the trough-delimiting surfaces 30 is selected to correspond to the angle of inclination of the side walls of the conveyor belt 24. The lower primary module 10 and upper primary module 12 are so dimensioned that they 10, 12 may be used with the largest belt sizes, as well as for much smaller belt sizes, for example one-half to one-third of the size of the large belt.

The upward facing surfaces of the lower modules 10, 14 and the upward facing surfaces of the replaceable side modules 18 include protruding alignment members 40 and the downward facing surfaces of the side modules 18, and the downward facing surfaces of the upper modules 12, 16 include alignment recesses 42 that complement the protruding alignment members 40 to assure accurate placement of the side modules 14 upon the lower modules 10, 14 and accurate placement of the upper modules 12, 16 upon the side modules 18. The alignment members 40 and the alignment recesses 42 are shown as generally convex bumps and concave dimples respectively. Alternatively, any form of male and female combination may be used, such as combinations of projections and sockets, ridges and grooves, pegs and holes, and tenons and mortises. Or, abutting module surfaces may have holes formed therein and a separate pin or dowel can be inserted into both holes as one module is lowered over and aligned with a another module. Generally placement and replacement of the modules is achieved by using a crane or other conventional lifting mechanism.

The replaceable liners 20, 21, 22 of neutron moderating and/or absorbing and/or reflecting material are placed adjacent the passageway 28 and adjacent the side modules 18 and/or the lower primary module 10 and/or the upper primary module 12 for further delimiting the passageway 28 and/or the bottom and/or the sides of the trough 34 to accommodate passage of the conveyor belt 24 through the passageway 28 in accordance with the size and shape of the conveyor belt 24. The sides of the liners 20, 21 that support the conveyor belt 24 have a low friction surface with good wear characteristics.

When it is necessary to accommodate passage of a flat conveyor belt, a liner 20 further delimiting the bottom portion of the trough 34 has an upper surface that is rounded upward from its longitudinal center (not shown) and/or the side liners 21 are shaped so that the side-of-the-trough-delimiting surfaces of the side liners 21 are vertical (not shown). In an alternative embodiment, the opposing surfaces 30 of the side modules 18 are vertical (not shown).

In some embodiments, the assembly does not include some or any of the replaceable liners 20, 21, 22 because the replaceable side modules 12 are so dimensioned and shaped that replaceable liners are not required for further delimiting the passageway 28 in order to better accommodate passage of the conveyor belt 24 therethrough or to enhance the uniformity of measurement sensitivity throughout the portion of the activation region that is occupied by the bulk material.

Referring to FIGS. 4A and 4B, a pair of replaceable sets of side modules 18a, 18b of different sizes and shapes are respectively placed between a given set of a lower primary module 10 and an upper primary module 12 for accommodating the passage of different sizes and shapes of conveyor belts 24a, 24b. The lower primary module 10 and the upper primary module 12 in the FIG. 4A embodiment are identical to the lower primary module 10 and the upper primary module 12 respectively in the FIG. 4B embodiment. The side modules 18a, 18b of each set are so dimensioned that said placement of the set of side modules 18a between the given set of the lower primary module 10 and the upper primary module 12, as shown in FIG. 4A, delimits the passageway 28a of the FIG. 4A embodiment to be of a different height and width than the height and width of the passageway 28b of the FIG. 4B embodiment, which is delimited by placement of the differently dimensioned set of side modules 18b between the given set of the lower primary module 10 and the upper primary module 12. As can be seen in FIGS. 4A and 4B, for larger belt widths increased spacing between the radiation source and the radiation detector is required. The replaceable-side-module assembly of the present invention enables increased spacing between the detector and source modules merely by replacing the side modules 18b of the FIG. 4B embodiment with the side modules 18a of the FIG. 4A embodiment. As the conveyor belt 24 becomes wider the side modules 18a also become narrower since the outside horizontal dimension of the overall assembly is constant over the full range of belt sizes. The outer dimensions of the overall assembly are such that for the largest belts, there is adequate space for shielding in the side modules 18a to keep the radiation emanating from the outside of the side modules to an acceptable level (usually 1 to 10 mR/hr). The thickness of the radiation shielding material in the side modules 18a, 18b may be determined either by computer modeling or empirically. The molds or fixtures for a family of assemblies includes one lower-module mold, one upper-module mold, and a set of side-module molds.

A plurality of sets of replaceable liners 20, 21, 22 of neutron moderating and/or absorbing and/or reflecting material also are provided for placement adjacent the side modules 18, and the lower module 10 at the sides and the bottom of the passageway 28, with the liners 20, 21, 22 of each set being so dimensioned that placement of different sets of liners 20, 21, 22 adjacent a given set of the side modules 18 and the lower module 10 respectively further delimit the passageway to different heights and widths to thereby enable one to compensate for small differences in the sizes and shapes of conveyor belts without having to replace the side modules 18.

Figure 5:
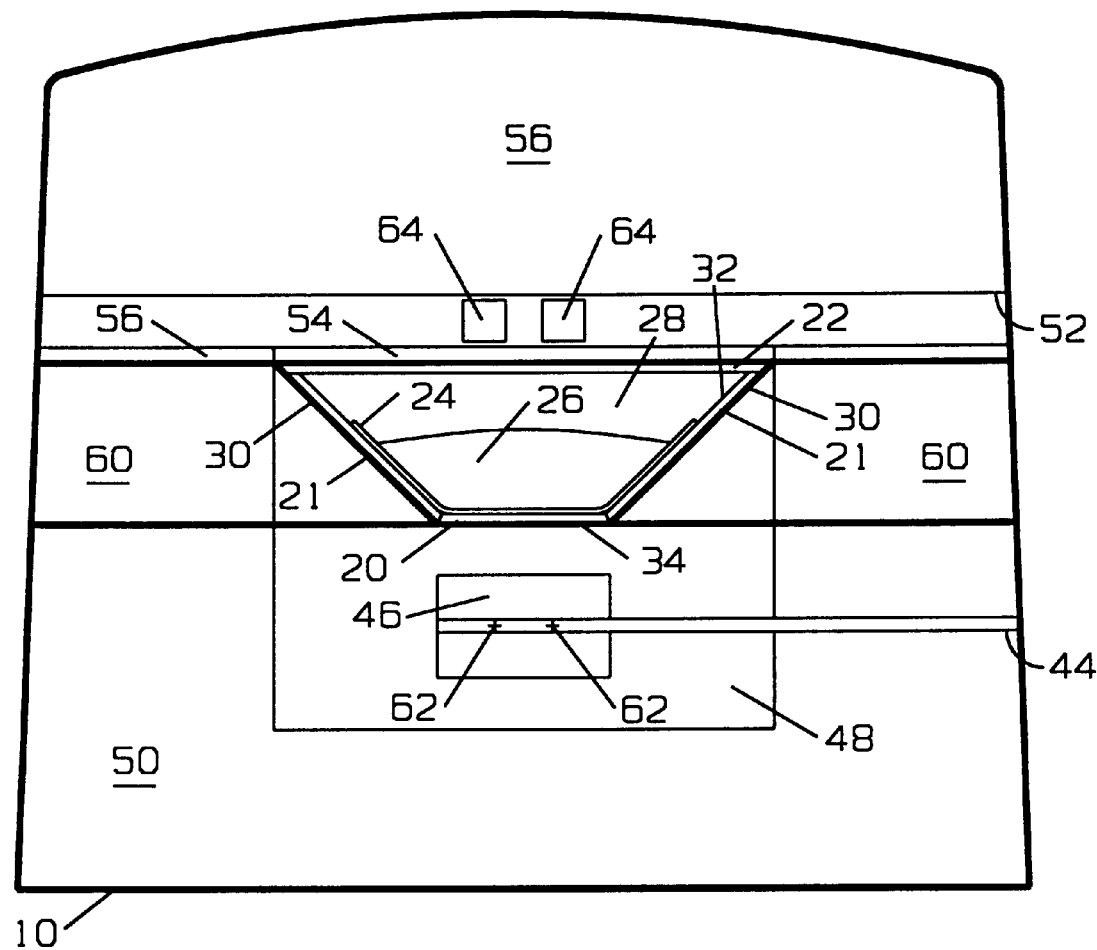
FIG. 5 is a sectional elevation view of an embodiment of the modules and liners included in the assembly of FIG. 1, with a conveyor belt passing through the assembly, wherein neutron sources are disposed below the passageway and gamma-ray detectors are disposed above the passageway, as taken along lines 5–5 through source and detector channels in the respective primary modules.
Figure 6:
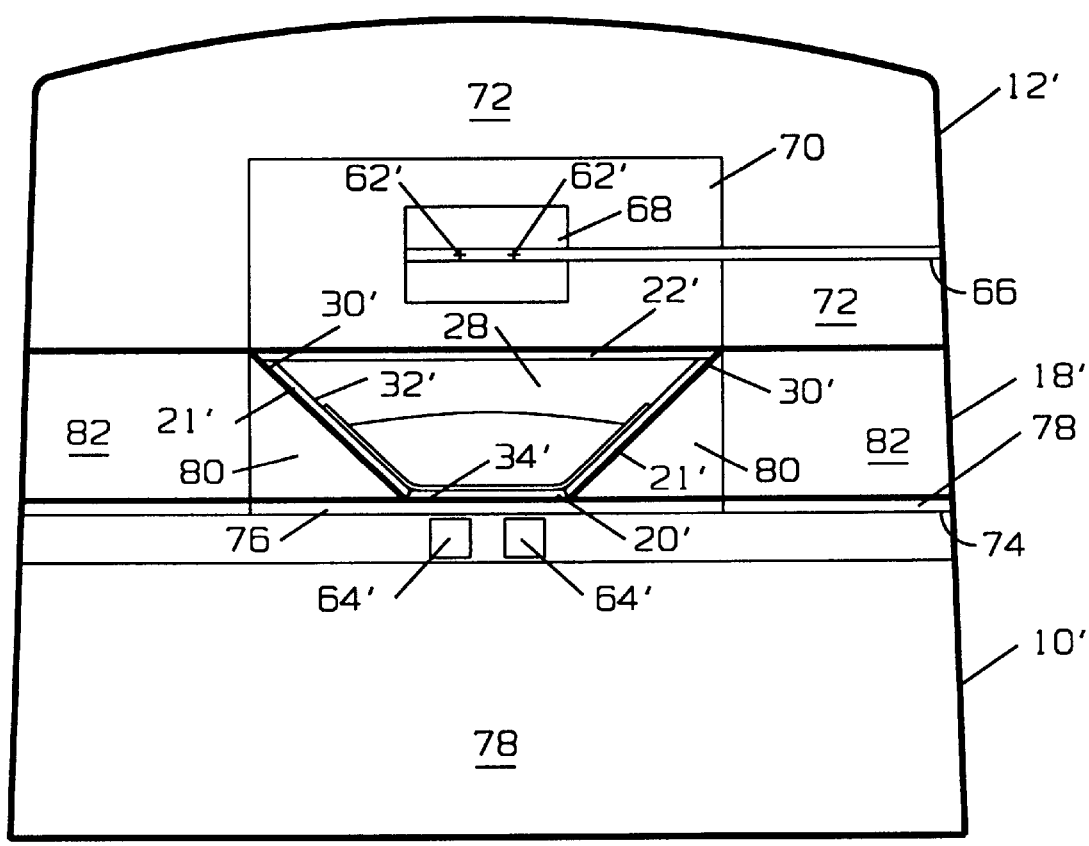
FIG. 6 is a sectional elevation view of an embodiment of the modules and liners included in the assembly of FIG. 1, with a conveyor belt passing through the assembly, wherein neutron sources are disposed above the passageway and gamma-ray detectors are disposed below the passageway, as also taken along lines 5–5 through source and detector channels in the respective primary modules.

The modular assembly of the present invention is used for bulk material analyzers of both the type in which neutron sources are disposed below the passageway and gamma-ray detectors are disposed above the passageway, as shown in FIG. 5, and the type in which neutron sources are disposed above the passageway and gamma-ray detectors are disposed below the passageway, as shown in FIG. 6.

In the embodiment of FIG. 5, the lower primary module 10 includes a source cavity 44, gamma-ray shielding material 46, neutron moderating material 48 and neutron shielding material 50; the upper primary module 12 includes a tubular detector channel 52, neutron reflecting material 54 and neutron shielding material 56; and each of the replaceable side modules 18 includes neutron moderating material 58 and neutron shielding material 60. Opposing surfaces 30 of the respective replaceable side modules 18 are shaped for delimiting the sides 32 of a trough 34 that is contoured with outwardly inclined side walls for accommodating passage of the conveyor belt 24 through the passageway 28.

A pair of neutron sources 62 are disposed in the source cavity 44 and a pair of gamma-ray detectors 64 are disposed in the detector channel 52. In an alternative embodiment, a plurality of such detector channels 52, 52', 52" are respectively likewise disposed in the upper primary module 12, as indicated in FIG. 2; and/or a plurality of such source channels 44 are respectively likewise disposed in the lower primary module 10.

The gamma-ray shielding material 46 reduces the number of gamma rays that reach the detectors 64 from the neutron sources 62. Preferably, the neutron sources 62 are Californium-252. In an alternative embodiment, electronic neutron sources 62 are provided.

The source cavity 44 is a tubular channel 44 disposed transverse to the longitudinal axis of the passageway 28 and approximately parallel to the bottom of the passageway 28. The source cavity 44 is only approximately parallel to the bottom of the passageway 28 in that the source cavity 44 may be inclined toward the sides of the lower module 10 from at or near a position beneath the longitudinal axis of passageway 28 by up to fifteen degrees from a plane that is parallel to the upper surface of the lower module 10. By providing such a moderate incline in the source cavity 44, the disposition of the sources 62 within the source cavity 44 may be varied in order vary the neutron moderation or shielding in accordance with the width of the conveyor belts 34.

One or more neutron sources 62 may be placed at variable positions within the source cavity 44 with respect to the longitudinal axis of the passageway :28. The gamma-ray shielding material 46 and the neutron moderating material 48 extend laterally, as shown in FIG. 5, so as to provide substantially the same amount of gamma-ray shielding material 46 and moderating material 48 between the sources 62 and the passageway 28 when the sources 62 are placed at different distances from the longitudinal axis of the passageway 28.

In an alternative embodiment (not shown), additional source cavities are disposed at different depths from the longitudinal axis of the passageway 28 so that the amount of neutron moderation provided by the neutron moderating material 48 can be varied by disposing one or more sources 62 in one or more selected source cavities.

The distance from the longitudinal axis of the passageway 28 at which the sources 62 are placed can be used to control the uniformity of measurement sensitivity throughout the bulk material 26 within the activation region. The position(s) of the neutron source(s) is determined through the use of computer modeling to optimize said uniformity of measurement sensitivity. For wider conveyor belts 24 it often will be found that if a source 62 is placed directly beneath the longitudinal axis of the passageway 28, there may be higher measurement sensitivity near the center of the passageway 28 than near the sides of the passageway 28. In such a case multiple sources 62 may be placed on opposite sides of a vertical plane extending through the longitudinal axis of the passageway 28 in order to optimize the uniformity of measurement sensitivity throughout the bulk material 26 within the activation region. Accordingly, several different conveyor belt sizes can be accommodated by having the above-described degree of freedom in the placement of the neutron sources 62 such that the same lower module 10 may be used for a wide range of belt sizes and a wide range of bulk material types and profiles. Typically, belt widths range from 60 to 140 centimeters. The neutron sources 62 can be placed in accordance with a wider range of belt widths.

The detector channel 52 is disposed transverse to the longitudinal axis of the passageway 28 and approximately parallel to the bottom of the passageway 28. The detector channel 52 is only approximately parallel to the bottom of the passageway 28 in that the detector channel 52 may be inclined toward the sides of the tipper module 12 from at or near a position above the longitudinal axis of passageway 28 by up to ten-to-fifteen degrees from a plane that is parallel to the lower surface of the upper module 12.

The detector channel 52 may be accessed though a door or a removable plug in at least one outside surface of the upper module 12 to thereby provide easy access to the detectors 64 for installation, adjustment, or replacement. One or more detectors 64 can be placed at any desired location in the detector channel 52.

Each of the detectors 64 has relatively uniform end-to-end sensitivity variations of less than one-half the energy resolution of the detector and is disposed in the channel 52 with its longitudinal axis disposed approximately parallel to the bottom of the passageway 28 and transverse to the longitudinal axis of the passageway 28. Two detectors may be placed end to end with their contact point in a vertical plane that extends through the longitudinal axis of the passageway 28 or they may disposed at opposite sides of said vertical plane. Means (not shown) are also disposed in the detector channel 52 to at least temporarily restrain the detectors 64 from movement within the detector channel 52 in response to acceleration or vibration of the upper module 12. If the detectors 64 were to be placed in a plane approximately parallel to the bottom of the passageway 28, but oriented with their longitudinal axes in the same longitudinal direction as the passageway 28, the detectors 64 would not be as accessible and the placement of the detectors 64 with respect to the vertical plane that extends through the longitudinal axis of the passageway 28 would also be limited.

The distance from the longitudinal axis of the passageway 28 at which the detectors 64 are placed can be used to control the uniformity of measurement sensitivity throughout the bulk material 26 within the activation region. The position(s) of the detector(s) is determined through the use of computer modeling to optimize said uniformity of measurement sensitivity. If, for example, it is found that the measurement sensitivity is higher at the vertical plane that extends through the longitudinal axis of the passageway 28 rather than toward the sides of the passageway 28, the detectors 64 may be moved within the detector channel 52 to be closer to the sides of the passageway 28 until a more uniform measurement sensitivity distribution is achieved. This optimal placement of the detectors 64 will be different for different width belts or flow channels, and/or for different types and profiles of bulk materials being analyzed. Accordingly, several different conveyor belt sizes can be accommodated by having the above-described degree of freedom in the placement of the detectors 64 such that the same upper module 12 may be used for a wide range of belt sizes and a wide range of bulk material types and profiles. The radiation detectors 64 can be placed in accordance with a wider range of belt widths than the typical belt widths range of from 60 to 140 centimeters.

The modular assembly of the present invention permits a single upper module design to be used for 1) different width belts, 2) for applications with different profiles of bulk material on the conveyor belt (i.e. flat, or humped in the middle) or 3) for different hydrogen content; and for each distinct application, the distance of the detector(s) 64 from the vertical plane that extends through the longitudinal axis of the passageway 28 may be optimized with no change to the mechanical design of the upper module 12.

The modular assembly of the present invention also easily by inexpensively adapts to different applications requiring different analytical precision. Greater precision is obtained with greater numbers of detected gamma-ray counts. The number of counts may be increased by increasing the source strength or detector size but this is limited by the maximum number of counts that may be easily handled by the detector electronics without distortion of the gamma ray spectrum, especially due to pile up. Once this level is reached, then the number of gamma-ray counts may be further increased by increasing the number of detectors. Typically, the repeatability of an analysis may be improved as the square root of the number of useful gamma-ray counts or the number of detectors. The modular assembly of the present invention readily accommodates placement of different numbers of detectors 64 in the upper module 12. For applications requiring less precision, cost may be saved by using a single detector 64 placed at an optimal location in the detector channel 52, as determined by computer modeling, that enables a measurement accurately representing the material flowing through the analyzer to be obtained even if the material on the conveyor belt 34 is not homogeneous in the lateral direction.

On the other hand, it is desirable to use two or more detectors 64 and/or more than one detector channel 52 for applications where higher count rates are required to achieve the required precision or when it is desirable to lessen the source strength in order to lower external radiation for regulatory reasons, while maintaining the precision. With smaller detectors 64 or ones whose length is only a small fraction of the length of the detector channel 52 more than two detectors 64 may be placed in each detector channel 52.

Replaceable liners 20, 21, 22 are placed adjacent the passageway 28 and adjacent the side modules 18, the lower primary module 10 and the upper primary module 12 for further delimiting the passageway 28 and the sides of the trough 34 to accommodate passage of the conveyor belt 24 through the passageway 28 in accordance with the size and shape of the conveyor belt 24. An individual liner on one or more sides of the passageway 28 may be varied in thickness and/or composition to fill the space between the bottom and side modules 10, 18 and the conveyor belt 24, and/or to optimize the moderation, absorption and/or reflection of neutrons to enhance the uniformity of measurement sensitivity throughout the portion of the activation region that is occupied by the bulk material. In some cases liners may comprise more than one material for a better optimization of a mechanical feature in combination with a particular neutron moderating, absorbing and/or reflecting, or gamma-ray absorption feature. For example, one might use a durable low friction layer of polyethylene overlaying a moderating material layer of bismuth for the bottom-of-the-trough liner 20 and the side liners 21.

The replaceable bottom-of-the-trough liner 20, which is placed adjacent the passageway 28 on the lower primary module 10 to further delimit the bottom of the trough 34, includes neutron moderating and/or absorbing material, as determined by computer modeling for enhancing the uniformity of measurement sensitivity throughout the cross-section of the bulk material 26 being analyzed within the activation region without having to modify the lower module 10 to accomplish such enhancement. Graphite is a preferred neutron moderating material; and boron in combination with a material having a high hydrogen content, such as polyethylene, is a preferred neutron absorbing material. In order to further enhance the uniformity of measurement sensitivity, the replaceable liner 20 may have a variable neutron moderating characteristic with respect to distance from the longitudinal axis of the passageway 28 and/or a variable neutron absorbing characteristic with respect to distance from the longitudinal axis of the passageway 28. Such variation may be accomplished by varying the thickness of the liner 20 or by variable inclusion of selected constituent neutron moderating and/or absorbing materials when it is desired to provide a liner 20 of uniform thickness; or both variation techniques may be combined in a single liner 20. Such a variable-thickness liner 20 varies in thickness from approximately 1.25 to 2.5 centimeters.

The thickness of the replaceable bottom-of-the-trough liner 20 is different for different circumstances. For example, when a small conveyor belt 24 is used or when the bulk material being analyzed has a low hydrogen content it is useful to increase the amount of neutron moderation provided by the bottom-of-the-trough liner 20 since the material being measured will provide little neutron moderation in those circumstances. Computer modeling is used to optimize the thickness and composition of the liner 20. Typically at least fifty percent by volume of the liner 20 is made of made of low neutron absorbing materials, such as graphite or bismuth, because of their low neutron absorption and good neutron moderating properties. In cases where additional neutron moderation in the bottom of the trough 34 is required for good uniformity of measurement sensitivity, the liner 20 may be made of a material that has a high hydrogen content, such as polyethylene. However, in those circumstances when the bulk material 26 being analyzed has a particularly high hydrogen content (over six percent), the liner 20 may be made of a thermal neutron absorbing material such as boron. The boron may be any form that is mechanically convenient. For example the boron can be dispersed in a polymer, such an epoxy, or in a material comprising primarily carbon, hydrogen and oxygen. Or the boron can be embodied in boric acid. The important point is that the thickness and composition of the liner 20 is easily and inexpensively modified to accommodate a wide range of belt sizes and a wide range of hydrogen content of the bulk material 26 being analyzed since no changes are required in the source or detector modules.

The replaceable side liners 21, which are placed adjacent the passageway 28 on the opposing surfaces 30 of the side modules 18 to further delimit the sides of the trough 34, include a neutron moderating and/or reflecting material, as determined by computer modeling in order to enhance the uniformity of measurement sensitivity throughout the cross-section of the bulk material 26 being analyzed within the activation region without having to modify the side modules 18 to accomplish such enhancement. A preferred neutron reflecting material is graphite, which has low neutron absorption, or bismuth, which also has a low neutron absorption characteristic and is a good gaimlma-ray absorber.

The replaceable top liner 22, is made of neutron reflecting material and is placed adjacent the passageway 28 on the upper primary module 12 when such placement is determined by computer modeling to be required for enhancing the uniformity of measurement sensitivity throughout the cross-section of the bulk material 26 being analyzed within the activation region without having to modify the upper module 12 to accomplish such enhancement. The top liner 22 is usually used to reflect neutrons to thereby increase the measurement sensitivity in top portion of the bulk material 26 on the conveyor belt 24, which top portion is nearest to the detectors 64. In order to enhance such sensitivity, the replaceable top liner 22 may have a variable neutron-reflecting characteristic with respect to distance from the longitudinal axis of the passageway 28. Such variation may be accomplished by varying the thickness of the top liner 22 or by variable inclusion of selected constituent neutron reflecting material when it is desired to provide a top liner 22 of uniform thickness; or both variation techniques may be combined in a single liner 22. The top liner 22 need not be of either the same composition or thickness at all distances from the longitudinal axis of the passageway 28. For example, more polyethylene may be placed nearer the ends of the top liner 22, which are farthest from the longitudinal axis of the passageway 28, in order to raise the measurement sensitivity near the sides of the passageway 28. If, on the other hand, computer modeling indicates that a greater measurement sensitivity is needed in the center of the passageway 28 more polyethylene is placed in the center portion of the top liner 22. A preferred neutron reflecting material for the liner nearest the detector(s) is polyethylene because of its high hydrogen content. Unlike the liners 21 that are used at the sides of the trough 34, the liner that is nearest the detector(s) need not have an especially low neutron absorption characteristic; and in some cases a higher neutron absorption characteristic may be helpful in protecting the detector(s) from excessive neutron flux.

Since the measurement sensitivity of a PGNAA bulk material analyzer is strongly affected by the distance between the neutron sources 62 and the gamma-ray detectors 64, it is preferable to provide the shortest separation distance between sources 62 and the detectors 64 that accommodates the greatest expected depth of bulk material on the conveyor belt 24. The top liner 22 may include different thicknesses of neutron reflecting material, as determined by computer modeling.

The number and placement of the neutron sources 62 and the gamma-ray detectors 64 and the particular selection, size, shape and placement of the neutron moderating materials 20, 21, 48, 58, the neutron absorbing material 20 and the neutron reflecting materials 22, 54 in the lower primary module 10, the upper primary module 12 and the side modules 18 in order to enhance measurement sensitivity throughout the portion of the activation region that is occupied by the bulk material are determined by computer modeling for a given conveyor belt size and shape and a given type and profile of bulk material and are in accordance with the teachings of U.S. Pat. No. 5,732,115 to Atwell et al. and U.S. patent application Ser. No. 08/882,075 filed by Hurwitz et al., both of which are assigned to the same assignee as the present application. The pertinent disclosures of both said patent and said patent application are incorporated herein by reference thereto.

The preferred computer modeling technique is described in a manual entitled "MCNP—A General Monte Carlo Code for Neutron and Photon Transport" published by the Radiation Shielding Information Center, P.O. Box 2008, Oak Ridge, Tenn. 37831. Such computer-aided modeling also takes into consideration attenuation of the gamma rays by the neutron moderating material disposed between the sampled bulk material and the detectors, by gamma-ray attenuating material variably disposed over the detector(s) and by the sampled bulk material itself.

The embodiment of FIG. 6 is sometimes preferred when the bulk material being analyzed has a high hydrogen content, such as over four percent by weight. Coal often has such a high hydrogen content by reason of having a high hydrogen content in combination of the organic material in the coal.

In the embodiment of FIG. 6, the upper primary module 12' includes a source cavity 66, gamma-ray shielding material 68, neutron moderating material 70 and neutron shielding material 72; the lower primary module 10' includes a detector channel 74, neutron reflecting material 76 and neutron shielding material 78; and each of the replaceable side modules 18' includes a section of neutron reflecting and shielding material 80 and a section of neutron shielding material 82. Preferably, the neutron reflecting and shielding material 80 is a mixture of boron and a hydrogenous material, such as borated polyethylene. Alternatively, a layer of neutron reflecting material (not shown) may overlie the section of the neutron reflecting and shielding material 80 at the surface 30' of each side module 18', in accordance with whatever neutron reflection is required for optimizing the uniformity of measurement sensitivity throughout the bulk material 26 within the activation region 28, as determined by computer modeling.

The source cavity 66 and the detector channel 74 are respectively disposed in the upper primary module 12' and the lower primary module 10' in the same manner as the source cavity 44 and the detector channel 52 are disposed in the lower primary module 10 and the upper primary module 12 in the embodiment described above with reference to FIG. 5 or in the alternative embodiments thereto also discussed above.

A pair of neutron sources 62' are disposed in the source cavity 66 and a pair of gamma-ray detectors 64' are disposed in the detector channel 74.

Opposing surfaces 30' of the respective replaceable side modules 18 are shaped for delimiting the sides 32' of a trough 34' that is contoured with outwardly inclined side walls for accommodating passage of the conveyor belt 24 through the passageway 28.

Conveyor belts 24 that typically are used to transport bulk material 26 through a bulk material analyzer usually have a high proportion of hydrogen, which acts as an excellent reflector of neutrons and thus increases measurement sensitivity in the portion that is closest to the detectors 64'. This is especially helpful where the depth of bulk material 26 is greater than eight inches (twenty centimeters).

Replaceable liners 20', 21', 22' are placed adjacent the passageway 28 and adjacent the side modules 18', the lower primary module 10' and the upper primary module 12' for further delimiting the passageway 28 and the sides of the trough 34' to accommodate passage of the conveyor belt 24 through the passageway 28 in accordance with the size and shape of the conveyor belt 24. An individual liner on one or more sides of the passageway 28 may be varied in thickness and/or composition to fill the space between the lower and side modules 10', 18' and the conveyor belt 24, and/or to optimize the moderation, absorption and/or reflection of neutrons to enhance the uniformity of measurement sensitivity throughout the portion of the activation region that is occupied by the bulk material.

The replaceable bottom-of-the-trough liner 20', which is placed adjacent the passageway 28 on the lower primary module 10' to further delimit the bottom of the trough 34', includes neutron reflecting material, as determined by computer modeling for enhancing the uniformity of measurement sensitivity throughout the cross-section of the bulk material 26 being analyzed within the activation region without having to modify the lower module 10' to accomplish such enhancement.

The replaceable side liners 21', which are placed adjacent the passageway 28 on the opposing surfaces 30' of the side modules 18' to further delimit the sides of the trough 34', also include a neutron reflecting material, as determined by computer modeling in order to enhance the uniformity of measurement sensitivity throughout the cross-section of the bulk material 26 being analyzed within the activation region without having to modify the side modules 18' to accomplish such enhancement.

The replaceable top liner 22', is made of neutron moderating and/or absorbing material and is placed adjacent the passageway 28 on the upper primary module 12 when such placement is determined by computer modeling to be required for enhancing the uniformity of measurement sensitivity throughout the cross-section of the bulk material 26 being analyzed within the activation region without having to modify the upper module 12 to accomplish such enhancement.

The embodiment of FIG. 6 also includes those other above-described features of the embodiment if FIG. 5 that are not incompatible with the above-described features of the embodiment of FIG. 6; and alternative embodiments of the embodiment of FIG. 6 may include the not-incompatible features of the alternative embodiments of FIG. 5 that are also discussed above.

The advantages specifically stated herein do not necessarily apply to every conceivable embodiment of the present invention. Further, such stated advantages of the present invention are only examples and should not be construed as the only advantages of the present invention. While the above description contains many specificities, these should not be construed as limitations on the scope of the present invention, but rather as examples of the preferred embodiments described herein. Other variations are possible and the scope of the present invention should be determined not by the embodiments described herein but rather by the claims and their legal equivalents.

We claim:

1. An assembly for analysis of bulk material moving through an analysis region located between at least one radiation source and at least one radiation detector, the assembly comprising
   a first module containing radiation shielding material and including means for retaining the at least one radiation source;
   a second module containing radiation shielding material and including means for retaining the at least one radiation detector; and
   at least two replaceable modules, each containing radiation shielding material, sandwiched between the first module and the second module to separate the first module from the second module, with the at least two replaceable modules being separated, to delimit a passageway for movement of the bulk material through the analysis region.

2. An assembly according to claim 1, further comprising at least one replaceable liner placed on a said module to further delimit the passageway.

3. An assembly according to claim 2, wherein the at least one replaceable liner includes a material having a characteristic of at least one of neutron moderating, neutron absorbing or neutron reflecting.

4. An assembly for a bulk material analyzer of the type in which bulk material is transported through an activation region located between at least one radiation source and at least one radiation detector within the bulk material analyzer, said assembly comprising
   container means including means for retaining at least one radiation detector, and defining at least one radiation source cavity and a passageway disposed for enabling passage of bulk material through an activation region located between the at least one radiation source cavity and the means for retaining at least one radiation detector; and
   radiation shielding material disposed within the container means;
   wherein the container means comprise
   a first primary module containing a first portion of the radiation shielding material and either defining said at least one radiation source cavity or including said means for retaining at least one radiation detector;
   an second primary module containing a second portion of radiation shielding material and either defining or including the other of either said at least one radiation source cavity or said means for retaining at least one radiation detector that is not defined or included respectively in the first primary module; and
   a set of replaceable side modules containing additional portions of the radiation shielding material;
   wherein the first primary module, the secondary primary module and the replaceable side modules are so shaped that the passageway is delimited by placement of the side modules between the first primary module and the second primary module.

5. An assembly according to claim 4, wherein one side of the passageway is delimited by a portion of the first primary module.

6. An assembly according to claim 5, wherein another side of the passageway opposite from said one side is delimited by a portion of the second primary module.

7. An assembly according to claim 4, comprising a plurality of sets of said replaceable side modules, wherein the side modules of each set are so dimensioned that said placement of different sets of side modules between a given set of said first and second primary modules respectively delimit the passageway to different heights and widths.

8. An assembly according to claim 7, further comprising a plurality of sets of replaceable liners of neutron moderating and/or absorbing and/or reflecting material for placement adjacent to the passageway and adjacent to the side modules and/or the first module and/or the second module; wherein the liners of each set are so dimensioned that said placement of different sets of liners adjacent to a given set of side modules and/or the first module and/or the second module respectively further delimit the passageway to different heights and/or widths.

9. An assembly according to claim 7, further comprising a set of replaceable liners of neutron moderating and/or absorbing and/or reflecting material placed adjacent to the passageway and adjacent to the side modules and/or the first module and/or the second module.

10. An assembly according to claim 9, wherein at least one said replaceable liner has a variable neutron moderating characteristic with respect to distance from the longitudinal axis of the passageway.

11. An assembly according to claim 9, wherein at least one said replaceable liner has a variable neutron absorbing characteristic with respect to distance from the longitudinal axis of the passageway.

12. An assembly according to claim 9, wherein at least one said replaceable liner has a variable neutron reflecting characteristic with respect to distance from the longitudinal axis of the passageway.

13. An assembly for a bulk material analyzer of the type in which bulk material is transported on a conveyor belt through an activation region located between at least one radiation source and at least one radiation detector within the bulk material analyzer, said assembly comprising:
   container means including means for retaining at least one radiation detector, and defining at least one radiation source cavity and a passageway disposed for enabling passage of a conveyor belt through an activation region located between the at least one radiation source cavity and the means for retaining at least one radiation detector; and
   radiation shielding material disposed within the container means,
   wherein the container means comprise:
   a lower primary module containing a first portion of the radiation shielding material and either defining said at least one radiation source cavity or including said means for retaining at least one radiation detector;

an upper primary module containing a second portion of radiation shielding material and either defining or including the other of either said at least one radiation source cavity or said means for retaining at least one radiation detector that is not defined or included respectively in the lower primary module; and a set of replaceable side modules containing additional portions of the radiation shielding material;

wherein the lower primary module, the upper primary module and the replaceable side modules are so shaped that the passageway is delimited by placement of side modules upon the lower primary module and placement of the upper primary module upon at least some of the placed side modules; and wherein portions of at least a pair of the replaceable side modules are shaped for delimiting the sides of a trough that is contoured for accommodating passage of the conveyor belt through the activation region.

14. An assembly according to claim 13, wherein the bottom of the passageway is delimited by a bottom-of-the-trough portion of the lower primary module.

15. An assembly according to claim 14, wherein the top of the passageway is delimited by a portion of the upper primary module.

16. An assembly according to claim 13, wherein a replaceable liner of neutron moderating and/or absorbing material is placed adjacent to the passageway on the primary module that defines the at least one source cavity.

17. An assembly according to claim 16, wherein a replaceable liner of neutron reflecting material is placed adjacent to the passageway on the primary module that includes the means for retaining at least one radiation detector.

18. An assembly according to claim 17, wherein replaceable liners of neutron moderating material are placed on the trough-delimiting portions of the replaceable side modules.

19. An assembly according to claim 16, wherein replaceable liners of neutron moderating material are placed on the trough-delimiting portions of the replaceable side modules.

20. An assembly according to claim 16, wherein the replaceable liner has a variable neutron moderating characteristic with respect to distance from the longitudinal axis of the passageway.

21. An assembly according to claim 16, wherein the replaceable liner has a variable neutron absorbing characteristic with respect to distance from the longitudinal axis of the passageway.

22. An assembly according to claim 13, wherein a replaceable liner of neutron reflecting material is placed adjacent to the passageway on the primary module that includes the means for retaining at least one radiation detector.

23. An assembly according to claim 22, wherein replaceable liners of neutron moderating materials are placed on the trough-delimiting portions of the replaceable side modules.

24. An assembly according to claim 13, wherein the trough-delimiting portions of the replaceable side modules are inclined outwardly from the bottom of the passageway.

25. An assembly according to claim 24, further comprising replaceable liners placed on the trough-delimiting portions of the replaceable side modules;

wherein the liners are shaped to further delimit the trough to have vertical side walls.

26. An assembly according to claim 13, further comprising a replaceable liner placed on the lower primary module for delimiting the bottom of the trough;

wherein the trough-delimiting surface of liner is rounded upward from its longitudinal center.

27. An assembly according to claim 13, wherein the means for retaining at least one radiation detector includes a channel disposed approximately parallel to the bottom of the passageway and transverse to the longitudinal axis of the passageway.

28. An assembly according to claim 27, wherein at least one detector having relatively uniform end-to-end sensitivity variations of less than one-half the energy resolution of the detector is disposed in said channel with its longitudinal axis disposed approximately parallel to the bottom of the passageway and transverse to the longitudinal axis of the passageway.

29. An assembly according to claim 13, wherein the means for retaining at least one radiation detector includes a plurality of channels respectively disposed approximately parallel to the bottom of the passageway and transverse to the longitudinal axis of the passageway for retaining a plurality of detectors.

30. An assembly according to claim 29, wherein at least one detector having relatively uniform end-to-end sensitivity variations of less than one-half the energy resolution of the detector is disposed in each said channel with its longitudinal axis disposed approximately parallel to the bottom of the passageway and perpendicular to the longitudinal axis of the passageway.

31. An assembly according to claim 13, wherein a plurality of said source cavities are channels respectively disposed approximately parallel to the bottom of the passageway and transverse to the longitudinal axis of the passageway.

32. An assembly according to claim 13, comprising a plurality of sets of said replaceable side modules, wherein the side modules of each set are so dimensioned that said placement of different sets of side modules between a given set of said lower and upper primary modules respectively delimit the passageway to different heights and widths.

33. An assembly according to claim 32, further comprising a plurality of sets of replaceable liners of neutron moderating and/or absorbing and/or reflecting material for placement adjacent to the side modules and the lower module at the sides and the bottom of the passageway;

wherein the liners of each set are so dimensioned that said placement of different sets of liners adjacent to a given set of the side modules and the lower module respectively further delimit the passageway to different heights and widths.

34. An assembly according to claim 13, further comprising a pair of lower secondary modules for placement on opposite sides of the lower primary module along the path of the passageway and respectively containing additional portions of the radiation shielding material;

a pair of upper secondary modules for placement on opposite sides of the upper primary module along the path of the passageway and respectively containing additional portions of the radiation shielding material;

wherein at least one of the side modules is placed upon the lower primary module and the lower secondary modules, and the upper primary module and the upper secondary modules are placed upon the at least one side module.

35. An assembly for a bulk material analyzer of the type in which bulk material is transported on a conveyor belt through an activation region located between at least one radiation source and at least one radiation detector within the bulk material analyzer, container means include means for retaining at least one radiation detector, and define at least one radiation source cavity and a passageway disposed for enabling passage of a conveyor belt through an activation region located between the at least one radiation source cavity and the means for retaining at least one radiation detector; and radiation shielding material is disposed within the container means; and the container means comprise a lower primary module containing a first portion of the radiation shielding material and either defining said at least one radiation source cavity or including said means for retaining at least one radiation detector; and an upper primary module containing a second portion of radiation shielding material and either defining or including the other of either said at least one radiation source cavity or said means for retaining at least one radiation detector that is not defined or included respectively in the lower primary module; said assembly comprising a set of replaceable side modules containing additional portions of the radiation shielding material;

wherein the replaceable side modules are so shaped in relation to the lower primary module and the upper primary module that the passageway is delimited by placement of side modules upon the lower primary module and placement of the upper primary module upon at least some of the placed side modules; and wherein portions of at least a pair of the replaceable side modules are shaped for delimiting the sides of a trough that is contoured for accommodating passage of the conveyor belt through the activation region.

36. An assembly according to claim 35, wherein the trough-delimiting portions of the replaceable side modules are inclined outwardly from the bottom of the passageway.

37. An assembly according to claim 35, comprising a plurality of sets of said replaceable side modules, wherein the side modules of each set are so dimensioned that said placement of different sets of side modules between a given set of said lower and upper primary modules respectively delimit the passageway to different heights and widths.

38. An assembly according to claim 37, further comprising a plurality of sets of replaceable liners of neutron moderating and/or absorbing and/or reflecting material for placement adjacent to the side modules and the lower module at the sides and the bottom of the passageway; wherein the liners of each set are so dimensioned that said placement of different sets of liners a given set of the side modules and the lower module respectively further delimit the passageway to different heights and widths.

39. An assembly according to claim 35 for a said bulk material analyzer that further comprises a pair of lower secondary modules for placement on opposite sides of the lower primary module along the path of the passageway and respectively containing additional portions of the radiation shielding material; and a pair of upper secondary modules for placement on opposite sides of the upper primary module along the path of the passageway and respectively containing additional portions of the radiation shielding material, wherein at least one of the side modules is shaped and dimensioned for placement upon the lower primary module and the lower secondary modules, and for placement of the upper primary module and the upper secondary modules upon the at least one side module.

40. An assembly according to claim 35, further comprising a replaceable liner of neutron moderating material for placement adjacent to the passageway on the primary module that defines the at least one source cavity.

41. An assembly according to claim 40, wherein the replaceable liner has a variable neutron moderating characteristic with respect to distance from the longitudinal axis of the passageway.

42. An assembly according to claim 35, further comprising a replaceable liner of neutron absorbing material for placement adjacent to the passageway on the primary module that defines the at least one source cavity.

43. An assembly according to claim 42, wherein the replaceable liner has a variable neutron absorbing characteristic with respect to distance from the longitudinal axis of the passageway.

44. An assembly according to claim 35, further comprising a replaceable liner of neutron reflecting material for placement adjacent to the passageway on the primary module that includes said means for retaining at least one radiation detector.

45. An assembly according to claim 44, wherein the replaceable liner has a variable neutron reflecting characteristic with respect to distance from the longitudinal axis of the passageway.

46. An improved method of analyzing the composition of bulk material having a hydrogen content exceeding four percent by weight, comprising the steps of:

(a) transporting the bulk material on a conveyor belt through an activation region located between at least one neutron source and at least one gamma-ray detector; and (b) processing signals produced by the gamma-ray detector in response to gamma-rays secondarily emitted from the bulk material in response to bombardment of neutrons in order to determine the elemental content of the bulk material, wherein the improvement comprises the steps of:

(c) disposing the at least one neutron source above the conveyor belt;

(d) disposing the at least one gamma-ray detector below the conveyor belt; and (e) disposing a neutron reflecting material between the conveyor belt and the at least one gamma-ray detector.

47. An assembly for a bulk material analyzer of the type in which bulk material is transported on a conveyor belt through an activation region located between at least one neutron source and at least one gamma-ray detector within the bulk material analyzer, and in which signals produced by the gamma-ray detector in response to gamma-rays secondarily emitted from the bulk material in response to bombardment of neutrons are processed in order to determine the elemental content of the bulk material, said assembly comprising container means including means for retaining at least one radiation detector, and defining at least one radiation source cavity and a passageway disposed for enabling passage of a conveyor belt through an activation region located between the at least one radiation source cavity and the means for retaining at least one radiation detector; and radiation shielding material disposed within the container means;

wherein the at least one neutron source cavity is disposed above the passageway;

wherein the means for retaining at least one radiation detector is disposed below the passageway; and wherein a neutron reflecting material is disposed between the conveyor belt and the means for retaining at least one radiation detector.

48. An assembly for a bulk material analyzer of the type in which bulk material is transported through an activation region located between at least one radiation source and at least one radiation detector within the bulk material analyzer, and container means include means for retaining at least one radiation detector, and define at least one radiation source cavity and a passageway disposed for enabling passage of the bulk material through an activation region located between the at least one radiation source cavity and the means for retaining at least one radiation detector, said assembly comprising a replaceable liner of neutron moderating material for placement adjacent to the passageway on a surface of the container means;

wherein the liner has a variable neutron moderating characteristic with respect to distance from the longitudinal axis of the passageway.

49. An assembly for a bulk material analyzer of the type in which bulk material is transported through an activation region located between at least one radiation source and at least one radiation detector within the bulk material analyzer, and container means include means for retaining at least one radiation detector, and define at least one radiation source cavity and a passageway disposed for enabling passage of the bulk material through an activation region located between the at least one radiation source cavity and the means for retaining at least one radiation detector, said assembly comprising a replaceable liner of neutron absorbing material for placement adjacent to the passageway on a surface of the container means;

wherein the liner has a variable neutron absorbing characteristic with respect to distance from the longitudinal axis of the passageway.

50. An assembly for a bulk material analyzer of the type in which bulk material is transported through an activation region located between at least one radiation source and at least one radiation detector within the bulk material analyzer, and container means include means for retaining at least one radiation detector, and define at least one radiation source cavity and a passageway disposed for enabling passage of the bulk material through an activation region located between the at least one radiation source cavity and the means for retaining at least one radiation detector, said assembly comprising a replaceable liner of neutron reflecting material for placement adjacent to the passageway on a surface of the container means;

wherein the liner has a variable neutron reflecting characteristic with respect to distance from the longitudinal axis of the passageway.

51. An assembly for a bulk material analyzer of the type in which bulk material is transported on a conveyor belt through an activation region located between at least one radiation source and at least one radiation detector within the bulk material analyzer, said assembly comprising container means including means for retaining at least one radiation detector, and defining at least one radiation source cavity and a passageway disposed for enabling passage of a conveyor belt through an activation region located between the at least one radiation source cavity and the means for retaining at least one radiation detector;

wherein the means for retaining at least one radiation detector includes a channel disposed approximately parallel to the bottom of the passageway and transverse to the longitudinal axis of the passageway.

52. An assembly according to claim 51, wherein at least one detector having relatively uniform end-to-end sensitivity variations of less than one-half the energy resolution of the detector is disposed in said channel with its longitudinal axis disposed approximately parallel to the bottom of the passageway and transverse to the longitudinal axis of the passageway.

53. An assembly according to claim 51, wherein the means for retaining at least one radiation detector includes a plurality of channels respectively disposed approximately parallel to the bottom of the passageway and transverse to the longitudinal axis of the passageway.

54. An assembly according to claim 53, wherein at least one detector having relatively uniform end-to-end sensitivity variations of less than one-half the energy resolution of the detector is disposed in each said channel with its longitudinal axis disposed approximately parallel to the bottom of the passageway and perpendicular to the longitudinal axis of the passageway.

* * * * *